United States Patent
Nobileau

[19]
[11] Patent Number: 6,062,314
[45] Date of Patent: May 16, 2000

[54] TUBING HANGER AND TREE WITH HORIZONTAL FLOW AND ANNULUS PORTS

[75] Inventor: Philippe Nobileau, Nice, France

[73] Assignee: ABB Vetco Gray Inc., Houston, Tex.

[21] Appl. No.: 08/968,392

[22] Filed: Nov. 12, 1997

Related U.S. Application Data

[60] Provisional application No. 60/030,807, Nov. 14, 1996.
[51] Int. Cl.[7] .................................................. E21B 33/043
[52] U.S. Cl. .......................... 166/368; 166/88.1; 166/88.4
[58] Field of Search ................................... 166/368, 88.1, 166/89.1, 88.4

[56] References Cited

U.S. PATENT DOCUMENTS

| | | | |
|---|---|---|---|
| 2,546,638 | 3/1951 | Humason | 166/88.1 |
| 5,366,017 | 11/1994 | Voss, Jr. | 166/88.4 |
| 5,465,798 | 11/1995 | McConaughy et al. | |
| 5,544,707 | 8/1996 | Hopper et al. | |
| 5,555,935 | 9/1996 | Brammer et al. | |
| 5,865,250 | 2/1999 | Gariepy | 166/88.1 |
| 5,884,706 | 3/1999 | Edwards | 166/368 |

*Primary Examiner*—William Neuder
*Attorney, Agent, or Firm*—Felsman Bradley Vaden Gunter & Dillon, LLP; James E. Bradley

[57] ABSTRACT

A well production assembly includes a production tree which has a lateral production passage extending laterally from a vertical bore of the tree. A tubing hanger, also having a lateral production passage, lands in the tree, with the lateral passages registering with each other. The junction of the lateral passages has flat, tapered sealed areas which mate with one another. An annulus passage extends vertically through the tubing hanger offset from and parallel to the tubing hanger vertical production passage. The annulus passage also has a lateral passage which registers with the lateral passage formed in the tree. The annulus lateral passages have a flat seal area at their junction. The tubing hanger has a downward facing hydraulic connector which registers with an upward facing hydraulic connector located on a shoulder formed in the bore. Once mated, the connectors provide hydraulic or other auxiliary fluid communication to downhole equipment.

20 Claims, 5 Drawing Sheets

6,062,314

TUBING HANGER AND TREE WITH HORIZONTAL FLOW AND ANNULUS PORTS

This application claims benefit of Provisional Application No. 60/030,807 filed Nov. 14, 1996.

TECHNICAL FIELD

This invention relates in general to wellhead equipment, and in particular to a production tree having a tubing hanger therein, the tubing hanger and production tree having lateral production passages.

BACKGROUND ART

A conventional subsea wellhead assembly includes a wellhead housing which supports one or more casing hangers located at upper ends of strings of casing extending into the well. A tubing hanger lands in the wellhead housing above the casing hanger and supports a string of production tubing that extends through the smallest diameter casing. The tubing hanger has a production bore which is offset slightly from the longitudinal axis. An annulus bore also extends through the tubing hanger, parallel to and offset from the axis, for communicating the tubing annulus to above the tubing hanger. The annulus bore is needed during installation of the tubing hanger and tubing to establish circulation down the tubing and back up the annulus. After the well has been completed, a removable plug is installed in the annulus bore, then a production tree is mounted to the wellhead housing. Access through the production tree to the tubing may be made for various workover operations that are needed.

In the last few years, operators have begun installing a different type of wellhead assembly, referred to generally as a horizontal tree. In a horizontal tree, the tubing hanger lands in the tree, not in the wellhead housing located below the tree. The tubing hanger has a lateral flow passage extending from its vertical flow passage. The lateral flow passage registers with a lateral flow passage extending through a sidewall of the tree. Gallery seals are employed to seal the junction between the lateral production passages. The gallery seals comprise seal rings which are coaxial with the vertical axis, with one of the seals located above the lateral passage and the other located below. The lower seal necessarily will be of a smaller diameter than the upper seal in order to provide clearances for installation.

With the horizontal tree, a tubing hanger can be pulled through the horizontal tree without removing the tree. This cannot be done with a conventional tree. While this is an advantage, one disadvantage is the horizontal tree tubing hanger has inadequate room to utilize a vertical annulus passage extending through the tubing hanger as with a conventional tubing hanger. Instead, tubing annulus communication is accomplished generally by utilizing a bypass passage through the tree from below the tubing hanger and back into the tree above the tubing hanger. While a bypass passage is workable, it relies on a valve on the exterior for closing the annulus. Some operators believe that a removable plug installed within an annulus passage in a tubing hanger is safer than a valve.

Another disadvantage of a typical horizontal tree tubing hanger has to do with the need to communicate auxiliary fluid to downhole equipment. For example, downhole safety valves are used in a tubing string at some distance below the surface. A safety valve remains open so long as it is supplied with hydraulic fluid pressure. In the absence of fluid pressure, it will close. Consequently, if the production wellhead assembly is severely damaged, the well would be held under control through the safety valve. In conventional tree tubing hangers, passages are drilled through the tubing hanger from the upper end to the lower end. The upper ends of the hydraulic passages have connectors which mate with connectors on the tree to supply hydraulic fluid. In the horizontal tree, however, this cannot occur because the tubing hanger lands within the tree, not in the wellhead housing below.

Some manufacturers have drilled ports through the sidewall of the tree to communicate with hydraulic passages drilled within the tubing hanger. These manufacturers have employed gallery type seals to seal the junctions of the ports. This again requires a reduction in inner diameter of the bore of the tree. There may be several ports for auxiliary fluid passages, requiring several sets of gallery seals. U.S. Pat Nos. 5,465,794 and 5,555,935 show ports on the exterior of a tubing hanger that do not requires gallery seals. These ports locate on a spherical surface formed on the tubing hanger and in the bore of the tree.

SUMMARY OF THE INVENTION

In this invention, the tree is of a horizontal type, having a lateral production passage. A tubing hanger, also having a lateral production passage, lands in the tree. The tree has a seal area that surrounds the inlet of the lateral production passages which is flat and inclined relative to the axis. The tubing hanger also has a seal area which is flat and inclined and mates with the tree seal area. The mating flat surfaces obviate the need for gallery seals, allowing a larger bore at that area than in the prior art gallery seal type.

Preferably the tubing hanger has an annulus flow passage that is offset from and parallel to the vertical production passage in the tubing hanger. The vertical annulus passage may be accessed from above and will receive a removable plug after completion. Preferably a lateral passage extends laterally from the vertical annulus passage of the tubing hanger and registers with a lateral annulus passage formed in the tree. The mating openings of the tree annulus passage are on flat and inclined sealed areas formed on the tubing hanger and in the bore of the tree. The lateral annulus passage allows access to the annulus through a valve as an option.

The tree also has an auxiliary passage which extends through a sidewall of the tree and has an auxiliary connector which is located on an upward facing shoulder forming the bore of the tree. The tubing hanger has a downward facing hydraulic connector which telescopingly mates with the connector in the tree bore. The auxiliary passages lead to a downhole safety valve.

DESCRIPTION OF THE PREFERRED EMBODIMENT

Figure 1A:
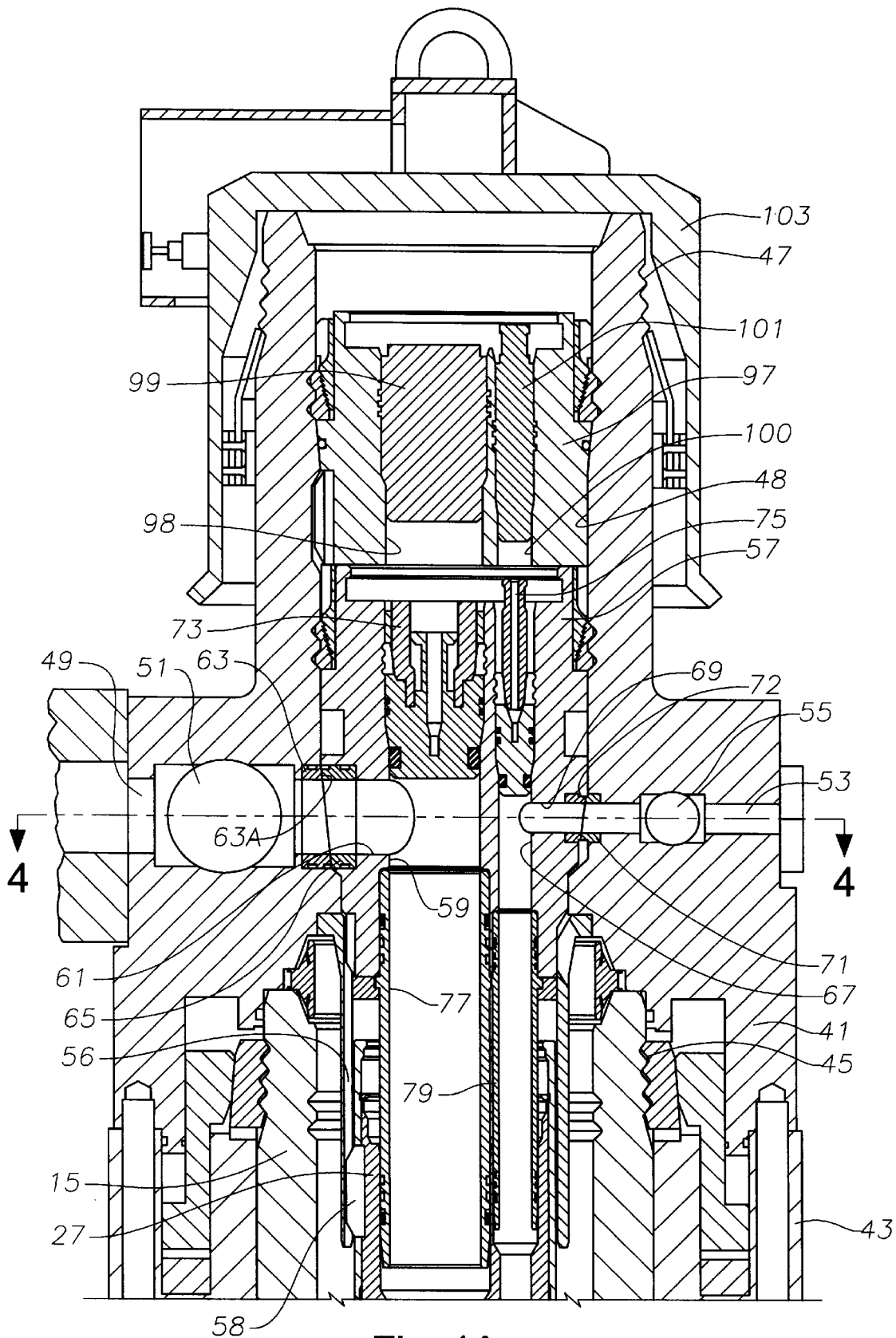
FIGS. 1A and 1B comprise a vertical sectional view of a wellhead assembly constructed in accordance with this invention.
Figure 1B:
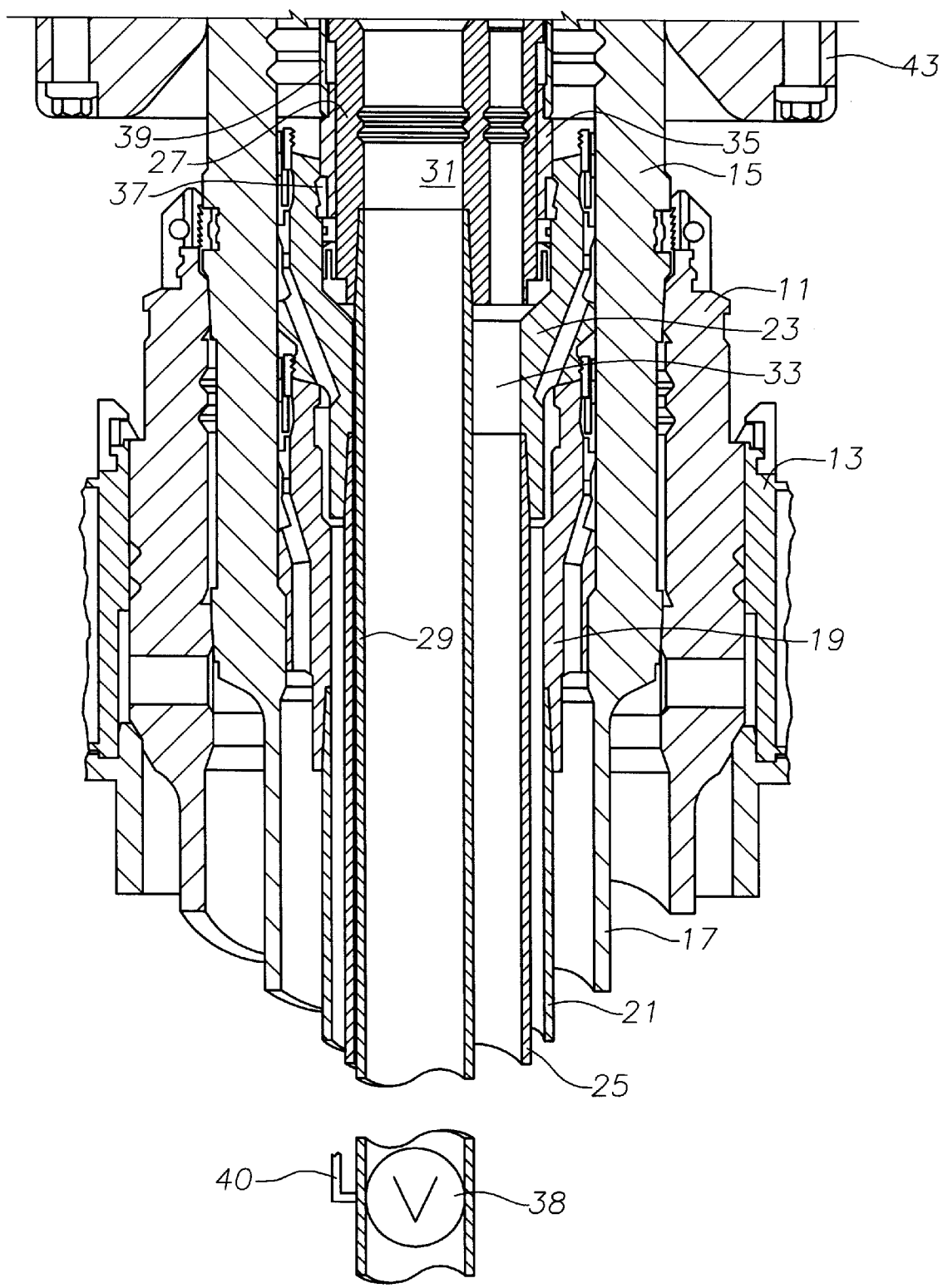

Referring to FIG. 1B, a subsea wellhead is shown, including a tubular low pressure housing 11 that lands in a guide base 13 supported on the sea floor. Housing 11 is connected to a large diameter conductor extending into the well to a first depth. A high pressure housing 15 lands in the low pressure housing 11. High pressure housing 15 is also a tubular member, and it is secured to a string of casing 17 which extends into the well to a second depth. A lower casing hanger 19 lands in wellhead housing 15 and supports a string of casing 21 which extends into the well to a third depth. An upper casing hanger 23 lands on top of lower casing hanger 19 and supports a string of casing 25 which extends to the bottom of the well in the embodiment shown. Both casing hangers 19, 23 are conventionally sealed to the bore of high pressure housing 15.

A lower tubing hanger 27 lands in the bowl of the upper casing hanger 23. Lower tubing hanger 27 is secured to a string of production tubing 29 which extends into the well for providing a conduit for the flow of production fluid. Lower tubing hanger 27 has a vertical production passage 31 which is coaxial with tubing 29. An annulus passage 33 is also axial or vertical, and extends alongside production passage 31. Annulus passage 33 is in communication with an annulus space surrounding tubing 29.

Lower tubing hanger 27 is secured conventionally in upper casing hanger 23 by means of a cam sleeve 35, lock ring 37, and actuating sleeve 39. Actuating sleeve 39 extends upward above the upper end of lower tubing hanger 27, as shown in FIG. 1B, and can be shifted by a running tool between an upper released position and a lower locked position. A downhole safety valve 38 is located in tubing 29 some distance below wellhead housing 11. Safety valve 38 is connected to a hydraulic line 40 which extends upward to lower tubing hanger 27. Hydraulic pressure in line 40 maintains safety valve 38 in an open position. The absence of hydraulic pressure in line 40 causes safety valve 38 to close.

Referring also to FIG. 1A, a christmas tree 41 lands on top of wellhead housing 15. A conventional hydraulic connector 43 carried by tree 41 connects tree 41 to a grooved profile 45 formed on housing 15 near its upper end. Tree 41 is a large tubular member that has a grooved profile 47 on its upper end that is identical to wellhead profile 45. Tree 41 has a production passage 49 that is horizontal, perpendicular to the longitudinal axis, and extends from its bore 48 to the exterior. A production master valve 51 controls the flow of production fluid out tree horizontal passage 49. Tree 41 also has an annulus passage 53 that is horizontal and perpendicular to the vertical axis. In the embodiment shown, it is located 180 degrees from and is coaxial with horizontal passage 49. Tree annulus passage 53 also extends from the tree bore 48 to the exterior. An annulus valve 55 can be controlled from the surface for opening and closing annulus passage 53.

Figure 2:
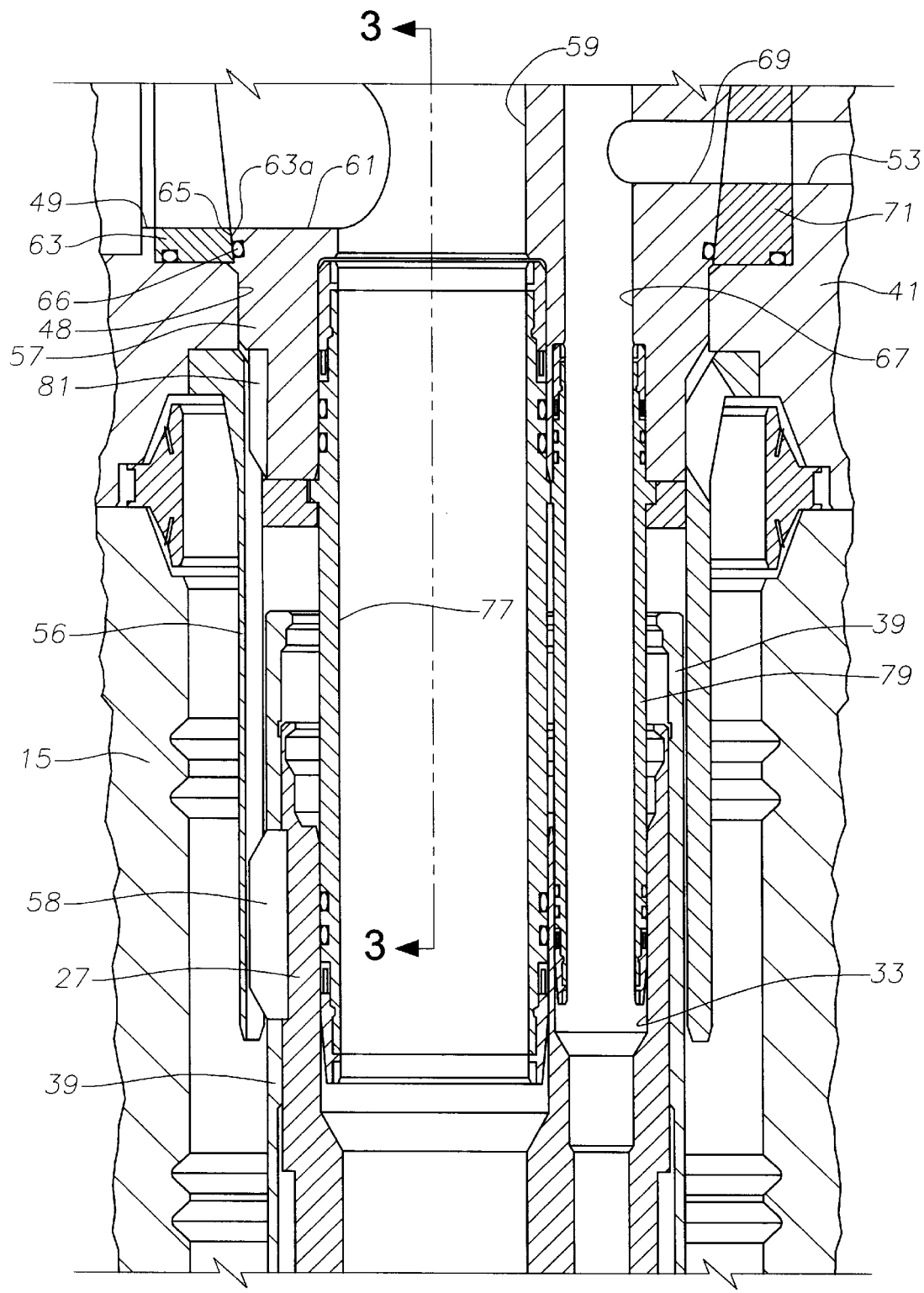
FIG. 2 is an enlarged partial sectional view of a portion of the wellhead assembly of FIGS. 1A, 1B.

Tree 41 is installed by lowering it on guidelines attached to guide posts (not shown) of guide base 13 in a conventional manner. As shown in FIG. 2, tree 41 has an orientation sleeve 56 mounted to it that extends around actuating sleeve 39 of lower tubing hanger 27. A key 58 on the exterior of lower tubing hanger 27 engages a slot in orientation sleeve 56. Orientation sleeve 39 orients lower tubing hanger 27 if tubing hanger 27 is being installed after tree 41 has already been installed. If lower tubing hanger 27 is installed before tree 41 is installed, it will be oriented by a conventional method using an orientation internal groove on the BOP stack wellhead connector.

Referring again to FIG. 1A, an upper tubing hanger 57 is supported in the bore of tree 41. Upper tubing hanger 57 has a vertical bore 59 that extends through it offset from and parallel to the longitudinal axis of tree 41. A lateral passage 61 extends horizontally outward from vertical bore 59 perpendicular to the vertical axis. A seat ring 63 is mounted in a counterbore in tree horizontal production passage 49 at the junction with tree bore 48. Seat ring 63 is sealed to passage 49 and has a hole through it that is the same diameter as passage 49. Seat ring 63 has an inner face 63a that is flat but inclined relative to the axis of tree 41. The upper edge of inner face 63a is farther from the axis of tree 41 than its lower edge. Seat ring 63 is sealed to passage 49 but is removable. Upper tubing hanger 57 has a mating seat ring 65 with a flat inclined outer face that is located at the outer end of lateral passage 61. Seat ring 65 seals against flat face 63a of seat ring 63 in metal-to-metal sealing engagement.

Similarly, upper tubing hanger 57 has an annulus vertical bore 67 which extends completely through upper tubing hanger 57 offset from and perpendicular to vertical bore 59. An annulus passage 69 extends horizontally from vertical bore 67. A seat ring 71 locates sealingly in a counterbore formed in tree annulus passage 53 at the junction with tree bore 48. Seat ring 71 is constructed the same as seat ring 63, except that its hole is smaller because the tree annulus passage 53 is smaller in diameter than the production passage 49. Upper tubing hanger 57 has a seat ring 72 that sealingly mates with the flat inclined face of seat ring 71.

A crown plug 73 of a conventional wireline retrievable type is installed in upper tubing hanger vertical bore 59. Crown plug 73 is located above horizontal passages 61, 49. An annulus plug 75, also wireline retrievable, is located in annulus vertical bore 67.

Referring to FIG. 2, a production isolation sleeve 77 is sealingly secured to the lower end of upper tubing hanger vertical production bore 59. Sleeve 77 extends sealingly into lower tubing hanger bore 31. An annulus isolation sleeve 79 secures sealingly to upper tubing hanger annulus bore 67. Annulus isolation sleeve 79 extends sealingly into lower tubing hanger annulus passage 33. Upper tubing hanger 57 has an orientation key 81, shown in FIG. 2, that engages orientation sleeve 56 of tree 41. This orients upper tubing hanger 57 relative to tree 41.

Figure 3:
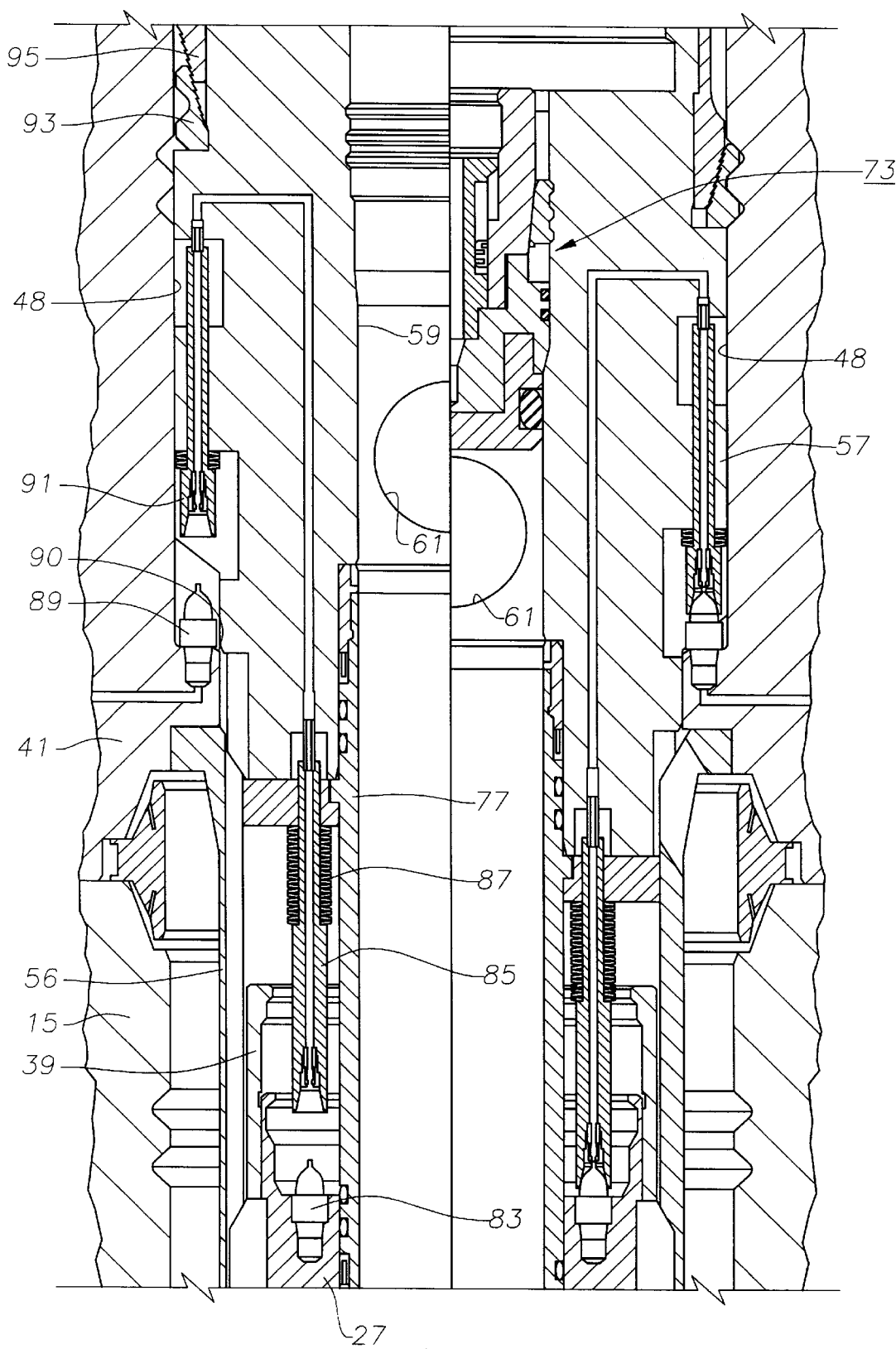
FIG. 3 is a sectional view of a portion of the wellhead assembly of FIGS. 1A, 1B, taken along the line 3—3 of FIG. 2, with the left side showing an installation step and the right side showing the assembly after installation has been completed.
Figure 4:
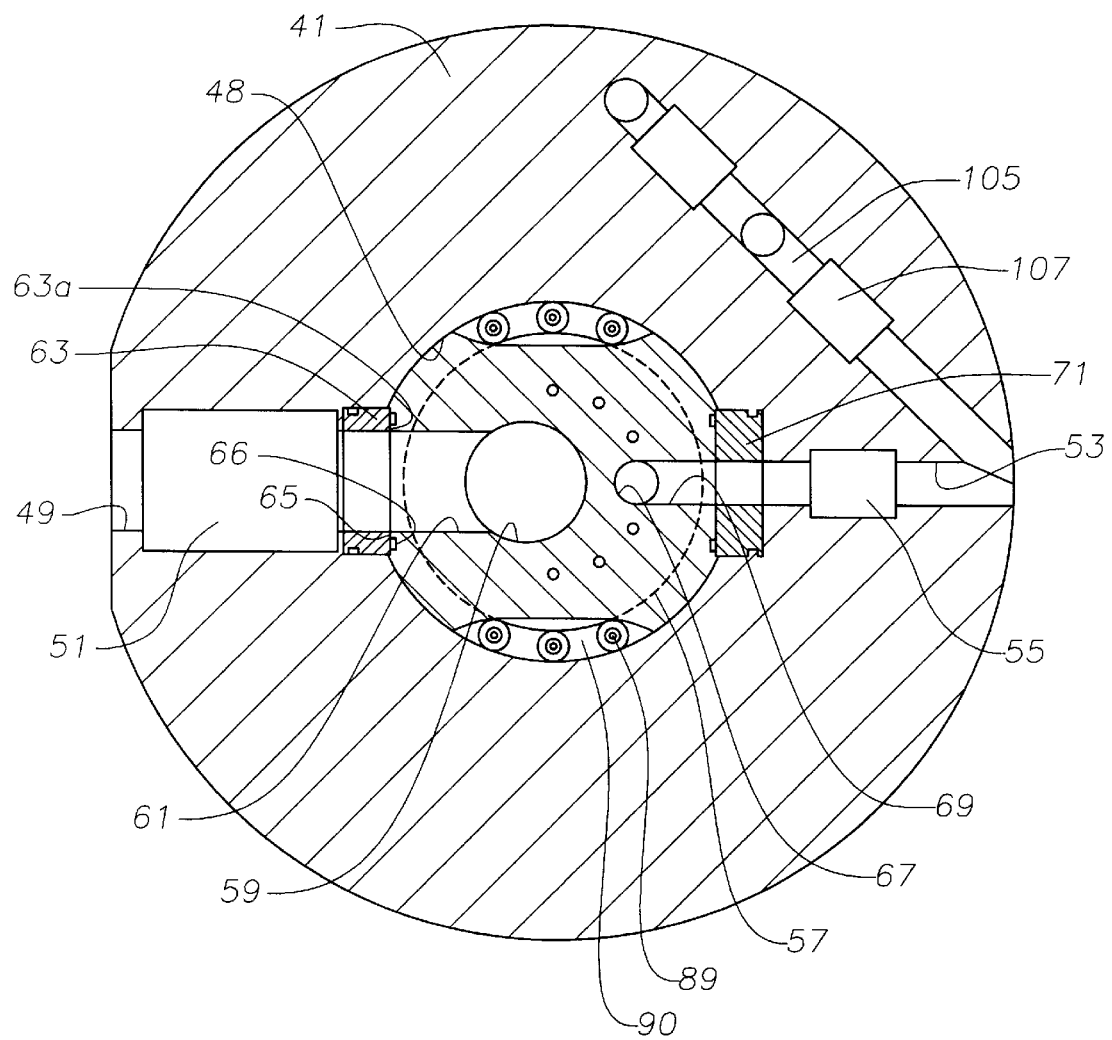
FIG. 4 is a sectional view of the wellhead assembly of FIGS. 1A, 1B, taken along the line 4—4 of FIG. 1.

Referring to FIG. 3, a plurality of hydraulic fittings or connectors 83 are mounted to lower tubing hanger 27 and face upwardly. Hydraulic connectors 83 connect to hydraulic lines 40 (FIG. 1B) for opening and closing downhole safety valves 38 (FIG. 1B). Female hydraulic fittings or connectors 83 are secured to the lower end of upper tubing hanger 57. Hydraulic connectors 85 will stab over hydraulic connectors 83 to make up a connection. Belleville springs 87 provide a positive pressure to retain the connection. Similarly, hydraulic connectors 89 are located on an upward facing shoulder 90 in bore 48 of tree 41 outside of where upper tubing hanger 57 will land. Downward facing female hydraulic connectors 91 are mounted to upper tubing hanger 57 to stab onto hydraulic connectors 89 when upper tubing hanger 57 is installed. Hydraulic connectors 89 are connected to passages which lead to a source of hydraulic fluid pressure for opening safety valve 38 (FIG. 1B) or performing other auxiliary functions. Connectors 89 are also shown in FIG. 4.

Referring to FIG. 3, upper tubing hanger 57 is secured in tree bore 48 by a lock member 93 which is pushed outward by a cam member 95. The left side of FIG. 3 shows upper tubing hanger 57 prior to insulation while the right side shows upper tubing hanger 57 after it is completely installed.

Referring again to FIG. 1A, an internal tree cap 97 locates within tree bore 48 above upper tubing hanger 57. Internal tree cap 97 has two vertical bores 98, 100 which align coaxially with the upper tubing hanger bores 59, 67. Wireline retrievable plugs 99, 101 are located within the bores 98, 100. A corrosion cap 103 is installed over the upper end of tree 41 for protection. Referring to FIG. 4, lateral annulus passage 53 leads to a crossover passage 105 which will selectively connect annulus passage 53 with the production passage 49. Valves 107 will control opening and closing of crossover passage 105.

In one mode of operation, after the well has been drilled and the casing hangers 19, 23 and lower tubing hanger 27 oriented and installed, the operator can run christmas tree 41 and secure it by connector 43. The operator then installs upper tubing hanger 57, which orients by means of its key 81 (FIG. 2) engaging tree orientation sleeve 56. After testing procedures, the operator installs wireline retrieval plugs 73, 75, internal tree cap 97, and wireline retrievable plugs 99, 101. The production fluid will flow up production tubing 29 and out horizontal passage 49.

Several workover options are available. In one mode, a drilling riser having a blowout preventer (not shown) will land on tree profile 47 after removing corrosion cap 103. The internal tree cap 97 is removed through the drilling riser using a recovery string extending through the riser. Closing the downhole safety valves (not shown) allows one to remove the wireline plugs 73, 75. An adapter on the recovery string stabs into the vertical production bore 59 while the annulus vertical bore 67 communicates with the drilling riser annulus around the recovery string and thus with the riser choke and kill lines once the blowout preventer is closed around the recovery string. One conduit leading to the production tubing 29 and one to the annulus space is then established with the workover vessel.

Prior to removing tubing 29, the well ordinarily must be killed. During this procedure, the well production fluid is replaced with a heavier fluid. The operator can kill the well by opening the downhole safety valve, and pumping down the recovery string and production tubing 29. The fluid flows out a port at the lower end of the production tubing 29, back up the tubing annulus, upper tubing hanger annulus bore 67, and up one of the choke and kill lines.

After the well is killed, the operator can retrieve production tubing 29 with the recovery string by pulling upper tubing hanger 57, then pulling tubing hanger 27 along with tubing 29. After the workover operation, tubing 29 and lower tubing hanger 27 are lowered through tree 41 and re-installed. Lower tubing hanger 27 will orient by engagement of key 58 with orientation sleeve 56 (FIG. 2) during the installation. Alternately, the operator may remove tree 41 without pulling tubing 29. In this instance, preferably another wireline plug (not shown) will be installed in a grooved profile in lower tubing hanger 27 before removing tree 41. When tree 41 is pulled upward, upper tubing hanger 57 and isolation sleeve 77 will be pulled with tree 41, while tubing hanger 27 and tubing 29 remain in place.

Further, the well may be killed in other manners than described above. Because of the two vertical bores 59 and 67 in upper tubing hanger 57, another method of killing involves stabbing a completion riser, which has two strings side by side, into these bores after removal of the internal tree cap 97 and plugs 73, 75. Also, killing of the well can be accomplished by use of the lateral annulus passage 69 and its crossover passage 105 (FIG. 4). In this situation, there will be no annulus conduit back to the vessel. Rather, after communication is established between the tubing hanger vertical passage 59 and the vessel, production master valve 51 is closed and annulus valves 55 and 107 (FIG. 4) are opened. Kill fluid is pumped down the production tubing 29, through a port (not shown) at the lower end and back up the tubing annulus. The return fluid flows out annulus horizontal passage 53, through crossover passage 105 and out the production line downstream of production master valve 51.

The wireline retrievable plugs 73 and 99 allow various wireline intervention operations without retrieving either tubing hanger 27, 57 or internal tree cap 97. During a wireline intervention when the well is not to be killed, downhole safety valve for tubing 29 will be closed to allow wireline plugs 99, 73 to be removed. The wireline tool will be lowered through a wireline riser which will be capable of withstanding the pressure of the well. The wireline riser comprises a wireline BOP stack mounted to tree 41 to control the well pressure. After the wireline tool has been lowered into tubing 29, the downhole safety valve is opened, allowing the wireline tool to pass through tubing 29.

The invention has significant advantages. Utilizing a flat seal area on the tubing hanger and in the bore of the tree avoids the need for gallery seals around the mating lateral passages. This allows a larger diameter tubing hanger for a particular tree bore than in the prior art. The larger diameter tubing hanger enables a vertical annulus passage to be drilled therein, which may be closed with a removable plug rather than a valve as in the prior art. The hydraulic connectors which mate when the tubing hanger lands also avoids the need for gallery seals.

It should be understood that variations to the embodiment may be made. For example, lower tubing hanger 27 may be eliminated. In that instance, upper tubing hanger 57 would connect directly to production tubing 29. It would not be possible to remove tree 41 without first pulling tubing 29, but it would be possible to pull tubing 29 without retrieving first the tree 41.

I claim:

1. A well production assembly located at an upper end of a string of tubing extending into a well, comprising:

a production tree having a longitudinal axis, an axial bore, and a lateral production passage, the lateral production passage having an inlet at the bore and extending laterally through a sidewall of the production tree;

a tree seal area in the bore surrounding the inlet of the lateral production passage, the tree seal area being flat and inclined relative to the axis;

a tubing hanger adapted to be located at an upper end of a string of tubing and landed in the bore, the tubing hanger having a vertical production passage extending through the tubing hanger and a lateral production passage which extends laterally from the vertical production passage and has an outlet at the exterior of the tubing hanger; and a tubing hanger seal area on the exterior of the tubing hanger surrounding the outlet of the lateral production passage, the tubing hanger seal area being flat and inclined relative to the axis and mating with the tree seal area, with the outlet registering with the inlet.

2. The well production assembly according to claim 1, further comprising:

a tree seat ring installed within the inlet of the lateral production passage of the tree, the tree seal area being located on an inward facing side of the tree seat ring.

3. The well production assembly according to claim 1, further comprising:

a tubing hanger seat ring installed within the outlet of the lateral production passage of the tubing hanger, the tubing hanger seal area being located on an outward facing side of the tubing hanger seat ring.

4. The well production assembly according to claim 1, further comprising:

a tree seat ring installed within the inlet of the lateral production passage of the tree, the tree seal area being located on an inward facing side of the tree seat ring; and a tubing hanger seat ring installed within the outlet of the lateral production passage of the tubing hanger, the tubing hanger seal area being located on an outward facing side of the tubing hanger seat ring.

5. The well production assembly according to claim 1, further comprising:

a vertical annulus passage extending axially through the tubing hanger offset from and parallel to the vertical production passage, the vertical annulus passage having a lower end in communication with a tubing annulus surrounding the string of tubing and an upper end at an upper end of the tubing hanger.

6. The well production assembly according to claim 1, further comprising:

a vertical annulus passage extending axially through the tubing hanger offset from and parallel to the vertical production passage, the vertical annulus passage having a lower end in communication with a tubing annulus surrounding the string of tubing;

a lateral annulus passage extending laterally through the tubing hanger from the vertical annulus passage, the lateral annulus passage having an opening on the exterior of the tubing hanger;

a tree annulus passage having an opening in the bore of the tree and extending laterally through the sidewall of the tree; and the openings of the lateral annulus passage and the tree annulus passage having mating annulus seal areas which are flat and inclined relative to the axis.

7. A well production assembly located at an upper end of a string of tubing extending into a well, comprising:

a production tree having a longitudinal axis, an axial bore, and a lateral production passage, the lateral production passage having an inlet at the bore and extending laterally through a sidewall of the production tree;

a tree seal area in the bore surrounding the inlet of the lateral production passage, the tree seal area being flat and inclined relative to the axis;

a tree auxiliary passage extending through the sidewall of the tree and having a tree auxiliary connector in the bore which faces generally upward;

a tubing hanger adapted to be located at an upper end of a string of tubing and landed in the bore, the tubing hanger having a vertical production passage extending through the tubing hanger and a lateral production passage which extends laterally from the vertical production passage and has an outlet at the exterior of the tubing hanger;

a tubing hanger seal area on the exterior of the tubing hanger surrounding the outlet of the lateral production passage, the tubing hanger seal area being flat and inclined relative to the axis and mating with the tree seal area, with the outlet registering with the inlet; and a tubing hanger auxiliary passage extending through the tubing hanger having a tubing hanger auxiliary connector on the exterior of the tubing hanger which faces generally downward and sealingly mates with the tree auxiliary connector as the tubing hanger lands in the production tree.

8. A well production assembly located at an upper end of a string of tubing extending into a well, comprising:

a production tree having a longitudinal axis, an axial bore and a lateral production passage, the lateral production passage having an inlet at the bore and extending laterally through a sidewall of the production tree;

a tubing hanger landed in the bore and adapted to be located at an upper end of a string of tubing, the tubing hanger having a vertical production passage extending through the tubing hanger and a lateral production passage which extends laterally from the vertical production passage through the tubing hanger and has an outlet at the exterior of the tubing hanger which registers with the inlet of the lateral production passage of the tree;

a vertical annulus passage extending through the tubing hanger from a lower end to an upper end of the tubing hanger offset from the vertical production passage, the vertical annulus passage having a lower end adapted to be in communication with a tubing annulus surrounding the string of tubing;

a removable production plug installed in the vertical production passage above the lateral production passage of the tubing hanger; and a removable annulus plug installed in the vertical annulus passage.

9. The well production assembly according to claim 8, further comprising:

a removable internal tree cap which sealingly engages the bore of the tree above the tubing hanger, the tree cap having a vertical production passage and a vertical annulus passage which are offset from and parallel to each other, the vertical production passage of the tree cap aligning with the vertical production passage of the tubing hanger, the vertical annulus passage of the tree cap aligning with the vertical annulus passage of the tubing hanger;

a removable production plug installed in the vertical production passage of the tree cap; and a removable annulus plug installed in the vertical annulus passage of the tree cap.

10. The well production assembly according to claim 8, further comprising:

a lateral annulus passage extending laterally through the tubing hanger from the vertical annulus passage, the lateral annulus passage having an opening on the exterior of the tubing hanger; and a tree annulus passage having an opening in the bore of the tree and extending laterally through the tree for sealingly registering with the opening of the lateral annulus passage of the tubing hanger.

11. The well production assembly according to claim 8, further comprising:

a tree seat ring installed within the inlet of the lateral production passage of the tree, the tree seat ring having a flat seal area located on an inward facing side of the tree seat ring, the seal area being inclined relative to the longitudinal axis; and a tubing hanger seat ring installed within the outlet of the lateral production passage of the tubing hanger, the tubing hanger seat ring having a flat seal area located on an outward facing side of the tubing hanger seat ring which sealingly engages the seal area on the tree seat ring.

12. A well production assembly, comprising:

a production tree having a longitudinal axis, an axial bore, and a lateral production passage, the lateral production passage having an inlet at the bore and extending laterally through a sidewall of the production tree;

a tree seat ring installed within the inlet of the lateral production passage of the tree, the tree seat ring having on an inward facing side a tree seal area which is flat and inclined relative to the axis;

a string of tubing extending into the well;

a tubing hanger connected to an upper end of the string of tubing and landed in the bore, the tubing hanger having a vertical production passage extending through the tubing hanger and a lateral production passage which extends laterally from the vertical production passage through the tubing hanger, the lateral production passage of the tubing hanger having an outlet at the exterior of the tubing hanger;

a tubing hanger seat ring installed the outlet of the lateral production passage of the tubing hanger, the tubing hanger seat ring having a tubing hanger seal area located on an outward facing side of the tubing hanger seat ring which sealingly mates with the tubing hanger seat ring;

a vertical annulus passage extending axially through the tubing hanger offset from and parallel to the vertical production passage, the vertical annulus passage having a lower end in communication with a tubing annulus surrounding the string of tubing and an upper end at an upper end of the tubing hanger;

a removable production plug installed in the vertical production passage above the lateral production passage; and a removable annulus plug installed in the vertical annulus passage.

13. The well production assembly according to claim 12, further comprising:

a lateral annulus passage extending laterally through the tubing hanger from the vertical annulus passage, the lateral annulus passage having an opening on the exterior of the tubing hanger;

a tree annulus passage having an opening in the bore of the tree and extending laterally through the tree; and the openings of the tubing hanger and the tree having mating annulus seal areas which are flat and inclined relative to the axis.

14. The well production assembly according to claim 12, further comprising:

a tree auxiliary passage extending through the sidewall of the tree and having a tree auxiliary connector in the bore which faces generally upward; and a tubing hanger auxiliary passage extending through the tubing hanger, having a tubing hanger auxiliary connector on the exterior of the tubing hanger which faces generally downward and sealingly mates with the tree auxiliary connector as the tubing hanger lands in the production tree to communicate the tree auxiliary passage with the tubing hanger auxiliary passage.

15. A well production assembly comprising in combination:

a production tree having a vertical axis, an axially extending bore, and a lateral production passage extending from the bore through a sidewall of the tree transverse to the vertical axis;

a generally upward facing shoulder formed in the bore;

a tree auxiliary passage extending through the sidewall of the tree and having an auxiliary connector located at the upward facing shoulder;

a string of tubing extending into a well;

a tubing hanger which lands sealingly in the bore and is connected to the string of tubing, the tubing hanger having a lateral production passage extending from a vertical production passage, the lateral production passage aligning with the lateral production passage of the tree; and a tubing hanger auxiliary passage extending through the tubing hanger, having an auxiliary connector which telescopingly and sealingly mates with the auxiliary connector in the tree when the tubing hanger lands, to communicate the tree auxiliary passage with the tubing hanger auxiliary passage.

16. The well production assembly according to claim 15, wherein each of the auxiliary connectors has an axis, and wherein the axes of the auxiliary connectors coincide when mated.

17. The well production assembly according to claim 15, wherein:

the auxiliary connector of the tree is a tubular member which protrudes upward from the upward facing shoulder; and the auxiliary connector of the tubing hanger is a tubular member which protrudes downward from the tubing hanger.

18. The well production assembly according to claim 15, wherein:

the auxiliary connector of the tree is a tubular member which protrudes upward from the upward facing shoulder; and the auxiliary connector of the tubing hanger is a tubular receptacle which protrudes downward from the tubing hanger and slides over the auxiliary connector.

19. The well production assembly according to claim 15, further comprising:

a downhole safety valve connected into the tubing string for selectively interrupting fluid flow through the tubing string; and a hydraulic line extending from the downhole safety valve to the tubing hanger auxiliary passage for receiving hydraulic fluid pressure from the tree auxiliary passage to actuate the downhole safety valve.

20. The well production assembly according to claim 15, wherein the auxiliary connectors of the production tree and the tubing hanger are parallel to the vertical axis.

* * * * *